(12) United States Patent
Tintelnot

(10) Patent No.: US 6,579,158 B2
(45) Date of Patent: Jun. 17, 2003

(54) FLEXIBLE, OPEN-PORED CLEANING BODY

(75) Inventor: Carl-Uwe Tintelnot, Weinheim (DE)

(73) Assignee: Firma Carl Freudenberg, Weinheim (DE)

( * ) Notice: Subject to any disclaimer, the term of this patent is extended or adjusted under 35 U.S.C. 154(b) by 204 days.

(21) Appl. No.: 09/876,703

(22) Filed: Jun. 7, 2001

(65) Prior Publication Data

US 2001/0041529 A1 Nov. 15, 2001

Related U.S. Application Data

(62) Division of application No. 09/620,183, filed on Jul. 20, 2000, now Pat. No. 6,422,933, which is a continuation of application No. 09/338,733, filed on Jun. 23, 1999, now Pat. No. 6,099,776, which is a division of application No. 08/964,300, filed on Nov. 4, 1997, now Pat. No. 5,971,841.

(51) Int. Cl.$^7$ .................................................. B24B 1/00
(52) U.S. Cl. ................................ 451/56; 451/66; 134/7
(58) Field of Search ................................ 451/526, 539, 451/532, 527, 528, 529, 530, 533, 56, 66; 134/7

(56) References Cited

U.S. PATENT DOCUMENTS

| 3,197,357 A | 7/1965 | Schulpen |
| 3,682,739 A | 8/1972 | Tesch et al. |
| 4,055,029 A | 10/1977 | Kalbow |
| 4,111,666 A | 9/1978 | Kalbow |
| 4,264,337 A | 4/1981 | Fenster et al. |
| 4,730,761 A | 3/1988 | Spano |
| 5,178,811 A | 1/1993 | Farley |
| 5,185,964 A | 2/1993 | Englund et al. |
| 5,190,568 A | 3/1993 | Tselesin |
| RE35,021 E | 8/1995 | Englund et al. |
| 5,681,217 A | 10/1997 | Hoopman et al. |
| 5,971,841 A | * 10/1999 | Tintelnot ..................... 451/526 |
| 6,099,776 A | * 8/2000 | Tintelnot ..................... 264/129 |
| 6,422,933 B1 | * 7/2002 | Tintelnot ..................... 451/526 |

FOREIGN PATENT DOCUMENTS

| DE | 76 12 130 | 4/1976 |
| DE | 27 30 266 | 1/1979 |

* cited by examiner

Primary Examiner—M. Rachuba
(74) Attorney, Agent, or Firm—Kenyon & Kenyon

(57) ABSTRACT

A flexible, open-pored cleaning body having at least one scouring surface (2) provided in at least one subregion with continuously formed, raised projecting ridges (3), wherein the ridges (3) have regions C,D of different heights in the direction of their extension.

14 Claims, 5 Drawing Sheets

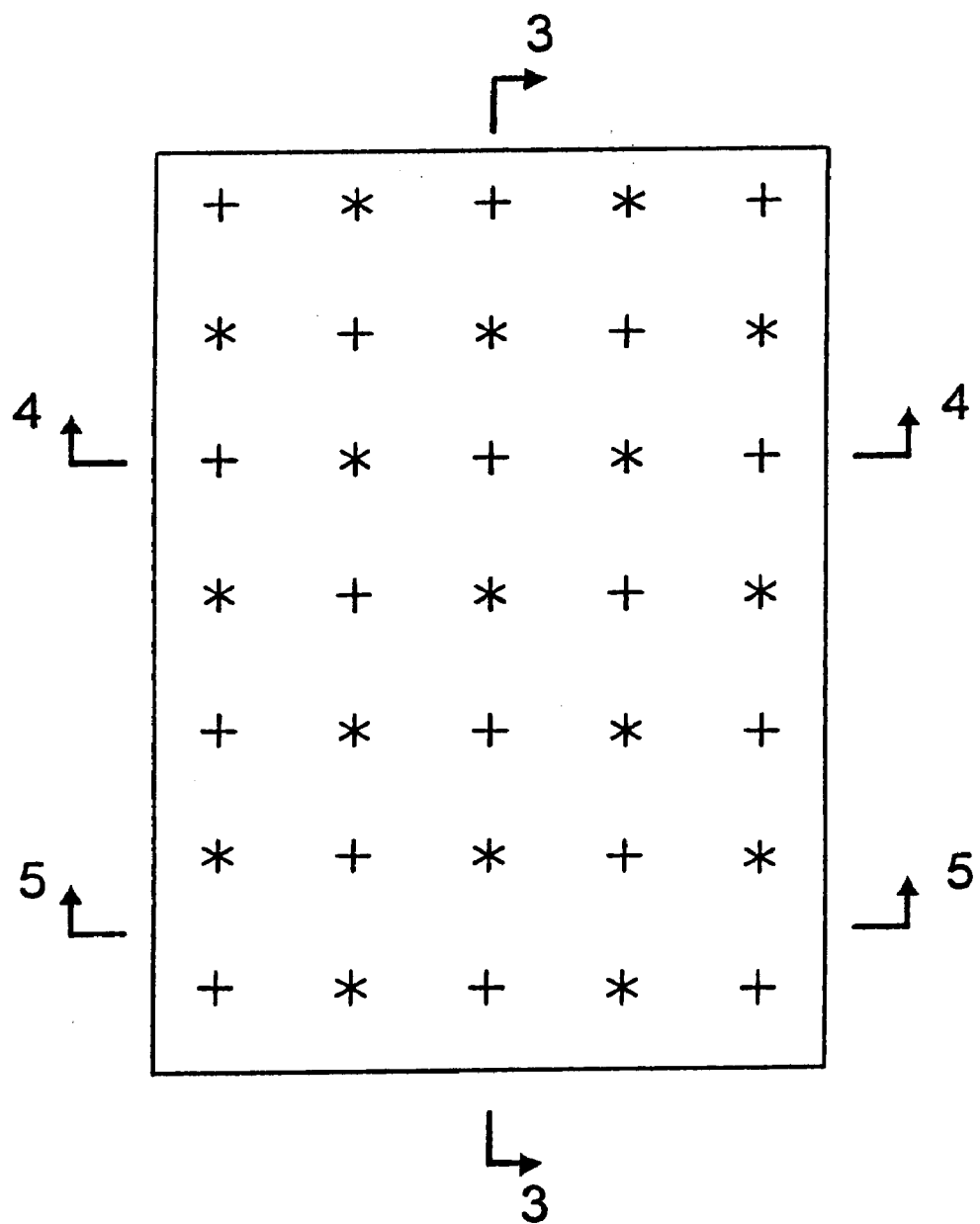
F I G. 2

FLEXIBLE, OPEN-PORED CLEANING BODY

CROSS-REFERENCE TO RELATED APPLICATIONS

This application is a division of prior application Ser. No. 09/620,183, filed Jul. 20, 2000, now U.S. Pat. No. 6,422,933 which is a continuation of prior application Ser. No. 09/338,733, filed Jun. 23, 1999, now U.S. Pat. No. 6,099,776, which is a division of prior application Ser. No. 08/964,300, filed Nov. 4, 1997, now U.S. Pat. No. 5,971,841.

FIELD OF THE INVENTION

The present invention relates to a flexible, open-pored cleaning body having at least one scrubbing surface which is provided in at least one subregion with continuously formed, raised projecting ridges.

BACKGROUND INFORMATION

A cleaning body is described in German Utility Patent No. 7 612 130. In the patent, the ridges have an identical cross-section over their entire length; they are arranged close to one another and separated from each other by perpendicularly incised channels. They consist of the same material as the cleaning body and have a correspondingly high flexibility. When encountering adherent solid dirt laterally, a lateral buckling is often observed, which makes little contribution to detaching the dirt and subsequently removing it. Besides, the already detached dirt components which penetrate into the interspaces between the ridges have a tendency to become fixed therein. They are hard to remove.

Another German Patent No. 27 30 266 describes cleaning bodies in which a plurality of isolated protuberances are arranged on a flat surface in close proximity to one another. Such cleaning bodies do not make it possible to wipe off a surface to be cleaned without leaving streaks. Further, the resistance of the protuberances to buckling decreases with increasing height. Thus, to remove adhering dirt, it is necessary to make the height of the protuberances very low. However, in so doing, an impairment of the dirt uptake capacity of the interspaces must be reckoned with.

SUMMARY OF THE INVENTION

An object of the present invention is to further develop a cleaning body in such a way that the mechanical removal of adhering dirt components can be achieved more satisfactorily than before.

According to the present invention, this task is accomplished with a flexible, open-pored cleaning body having at least one scrubbing surface which is provided in at least one subregion with continuously formed, raised projecting ridges.

It is provided for the cleaning body according to the present invention that the ridges are formed in a continuous manner and have regions of different heights in the direction of their extension. Here, the present invention is based on the recognition that, as a rule, the thickness of contaminations covering a surface to be cleaned is largely uniform. Their removal with the use of the cleaning body according to the invention is not intended to be done in a single step, but in such a way that the ridges attack the dirt only at the most protuberant sites of the cleaning body, which makes it possible to exert at these sites high specific contact pressures on the dirt through the ridges. In this way the breakup and removal of the dirt at isolated places and/or during the forward movement of the cleaning body in the course of isolated scraping is facilitated. It is advantageous that the raised sites of the ridges are connected with each other via zones which protrude to a lesser extent, and therefore in a position to carry out a supplementary windshield-wiper effect over their entire length. In this way, by moving the scrubbing agent to and fro in closely adjacent streaks over a surface to be cleaned and substantially transversely or obliquely to the direction of the ridges, complete removal of all dirt components adhering thereto is achieved within a short time. In addition, the areas of low height adjacent to the protuberances along the ridges provide said protuberances with static support against lateral buckling. As a result, the cleaning body is particularly suitable for use in the domestic or industrial sector.

The ridges normally extend parallel to each other. They can be designed so that they have a straight—line, serpentine or zig-zag course. A design in which the adjacent ridges are arranged so as to fill gaps, at least with regard to their protuberances, is also possible and can improve the cleaning effect. In their course, the ridges can successively change direction in an irregular manner, or be self-enclosing and have the form e.g. of a ring or ellipse.

With regard to its external shape, the cleaning body may be modified in various ways. For example, it is possible to give it the form of a cleaning cloth or a scrubbing sponge of parallelepiped shape.

Many possibilities exist also with regard to the materials used for fabricating the cleaning bodies. Apart from open-cell foams, fiber-containing materials such as fleeces or laminated materials, which optionally contain both foams and fibers, can also be used. In that case the foams and fibers can have a blended structure or be imbedded in one another.

If fibers are used, it is merely necessary to ensure that the titer of the fibers not be too low. Advantageously, the titer should be in the range of coarse staple fibers, at about 0.2 to 40 dtex, preferably between 1 and 6.7 dtex. A supplementary or alternative use of metallic fibers can also be included in the considerations.

Used as foams are primarily soft, open-pored, polyurethane flexible foams having a density of from 15 to 200 $kg/m^3$, preferably between 20 and 50 $kg/m^3$.

The use and preparation of the cleaning agent is particularly simple when the regions in which the ridges have a varying height regularly follow each other in a recurrent fashion.

According to an advantageous embodiment of the present invention, the regions of varying height are designed so that they blend into one another in a uniform manner. In this way the formation of streaks when wiping smooth surfaces can be avoided in a particularly simple way. Ridges in which the regions of varying height follow each other in a sinusoidal form are preferred.

To enable the cleaning body to be used in a way that is independent of the direction of the streaks during wiping processes, provision can be made for the ridges to cross one another. When a regular pattern is used, this offers the possibility of producing the ridges without any waste, in such a way that a thicker layer of the material forming the cleaning body is elastically deformed with the use of inflexible molding materials of relief-like structure, and then split into two identical cleaning bodies.

The mechanical resistance of the ridges to a lateral buckling movement can be increased if they, viewed in the transverse direction, are delimited by inclined surfaces. Viewed in the transverse position, these surfaces can have a curvature and optionally a sinusoidally blending profile.

The ridges are produced in one piece with the scrubbing agent made of the same material. Accordingly, in the case of unfavorable profiling, the mechanical strength under certain circumstances is very low. To improve this situation it has been found advantageous if the ratio between the distance of the midpoints of adjacent ridges and their maximum height is about 4 to 12, preferably from 6 to 9. Even with the use of relatively easily deformable materials, adherence to this ratio makes it possible to obtain an excellent wiping effect.

The scrubbing surface can be provided with a flexible coating which improves the abrasion resistance. Examples of coatings are described in U.S. Pat. No. 4,264,337. Within the framework of the present invention, a two-component polyurethane is preferentially used, which is cross-linked by subsequent heating and then hardened. In this way, the penetration of the protuberances of the scrubbing surface into adherent dirt layers is further improved. Advantageously, such a coating is applied to or pressed into the scrubbing surface in the liquid state, and then hardened. Particles of a scrubbing agent, e.g. particles of a rubber granulate and/or an abrasive grain, may optionally be embedded therein.

For speedy performance of cleaning processes it is highly advantageous if, during the cleaning process, the cleaning body can be used as a water-storing means and if it is possible to displace the water contained in the cleaning body e.g. by simple compression and then re-release it toward the front side of the scrubbing surface, or if it can be drawn away from it by suction. To meet this requirement, it has proved useful for the coating to be permeable to liquids and, e.g., be permeated by pores.

When the ridges are arranged obliquely to the longitudinal direction of the cleaning body, a wiper effect is obtained when it is used as specified, which makes it possible to quickly remove liquids from large surface areas.

Advantageously, the coating of the cleaning body is continuously applied to the scrubbing surface during an elastic deformation with the aid of a roll mill, pressed into it to an at least partial extent, and then hardened. In this way a particularly intimate bond results between the coating and the cleaning body, which improves the durability of the cleaning body.

Found particularly advantageous has been a process for fabricating the cleaning body from open-pored foam, a process wherein a substantially flat foam mat is elastically deformed in a continuous manner between intermeshing projections of a pair of rolls, and, within the roll slit, is divided by a straight cut into two mat sections, which, on emerging from the roll slit, are delimited on the opposite sides by a corrugated surface, with the individual cleaning bodies obtained by being punched out from the mat sections. This process operates without waste, and is thus advantageous from both the economical point of view and with regard to avoidance of waste materials.

In the aforementioned process a coating of liquid polymeric material, e.g. a solution of elastomeric polyurethane, is advantageously applied to the corrugated surface of the mat sections, and is then hardened. In this way, the coating still in the liquid state can be pressed into the mat section under continuous elastic deformation of said mat section. The application and pressing-in of the coating are most successful when the deformation is carried out with the aid of a roll mill, so that all surface zones of said mat section are included. By operating in this way, the coating surprisingly has a largely uniform layer density in all subregions of the corrugated surface of the cleaning body, even though rolls having a cylindrical surface can be used. The components of the coating situated in the region of protuberances and recesses of the scrubbing surface can thereby be mutually supported when transverse forces appear, a fact which improves the scrubbing effect and prevents detachment of the coating when abrasive stress is exerted on the protuberances. In general, the coating layer has a thickness of from 2 to 5 mm, of which only about 1 mm extends beyond the surface of the foamed body.

BRIEF DESCRIPTION OF THE DRAWINGS

FIG. 2 shows a scrubbing surface wherein the highest points of the ridges are marked with a star and the lowest points with a cross, and in which the position of the individual cutting planes according to FIGS. 3 to 5 are indicated.

DETAILED DESCRIPTION OF THE INVENTION

Figure 1:
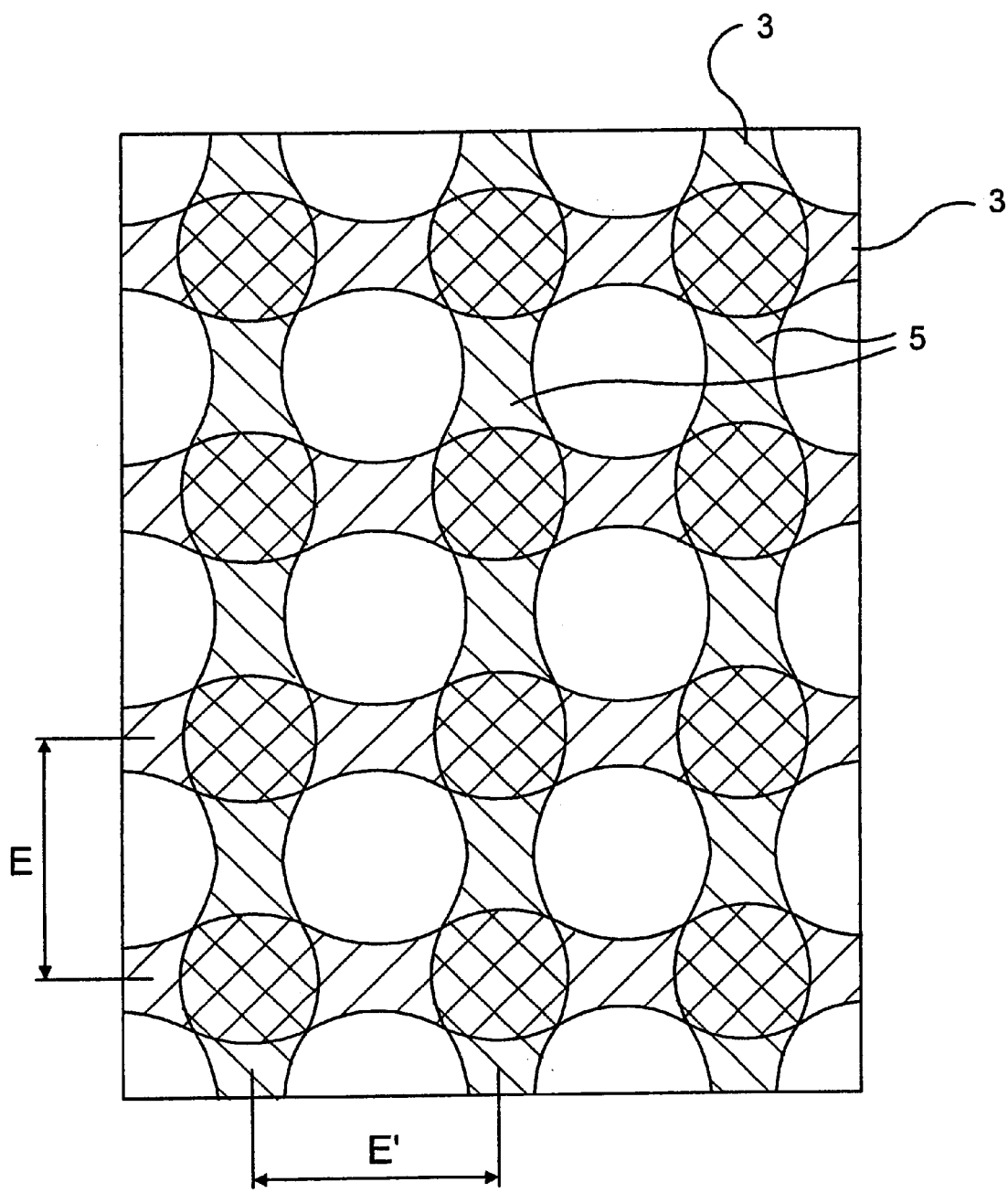
FIG. 1 shows a view of the scrubbing surface of a typical cleaning body according to the present invention.

In the drawing, the scrubbing surface of a cleaning body shown by way of example is represented in top view. In the area of the scrubbing surface 2 (FIGS. 3 and 4), the cleaning body is comprised of a foam material 1 of open-pored polyurethane foam having a bulk density of between 20 and 50 kg/m$^3$. On its top surface 4 (FIG. 3) continuous raised ridges 3 are arranged so as to form the scrubbing surface 2, said ridges forming two perpendicularly intersecting ridge clusters. The ridge clusters form a one-piece component of the foam material 1 forming the cleaning body in the region of the upper side. They are produced by a cutting process in a waste-free manner.

Figure 3:
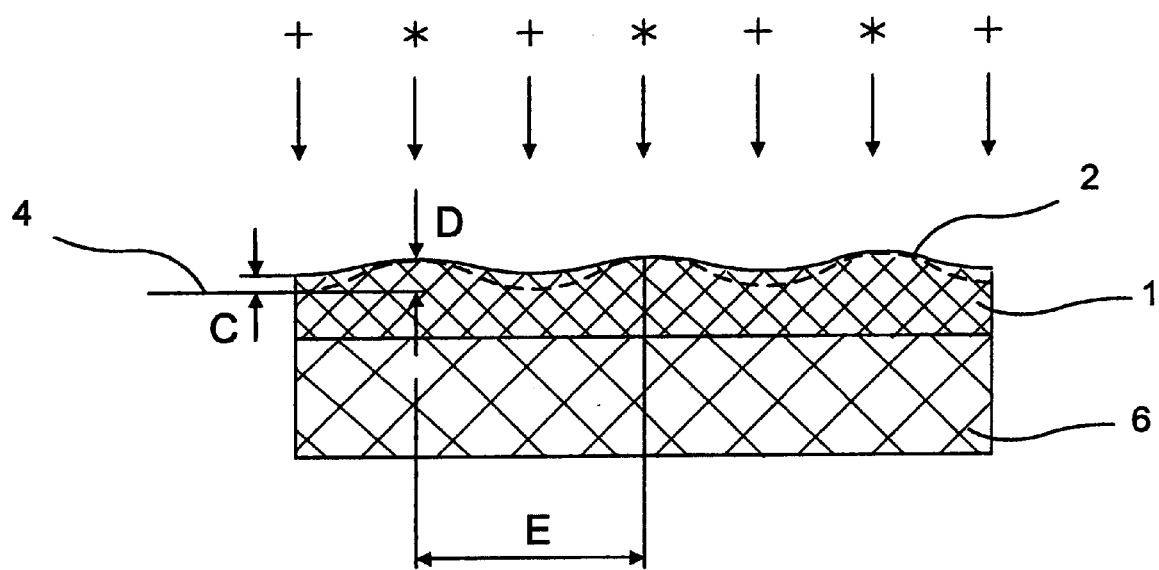
FIG. 3 shows the cleaning body according to FIG. 1 in sectional representation.
Figure 4:
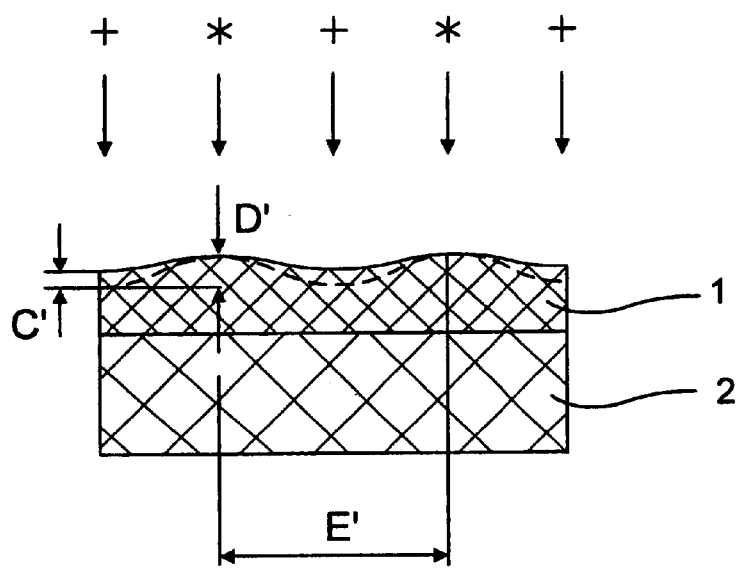
FIG. 4 shows the cleaning body according to FIG. 1 in another sectional representation.
Figure 5:
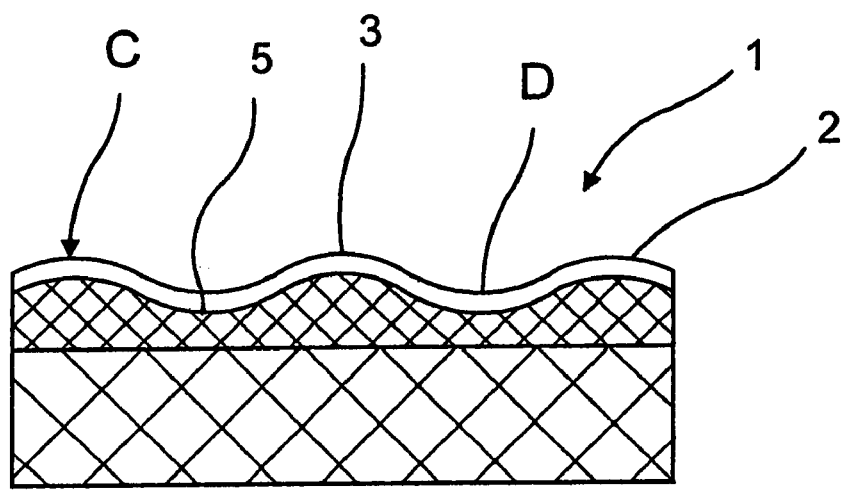
FIG. 5 shows the cleaning body according to FIG. 1 in yet another sectional representation.

Within both ridge clusters, the distance between opposite midpoints of adjacent ridges 3 is 30 mm, at a maximum height of 4 mm and a minimum height of 2 mm, in each case in terms of that site of the profile where the latter attains its greatest distance from an imaginary prolongation of the top surface 4. The spatial position of the top surface is indicated in FIG. 3. The dimensioning can be varied as a function of the specific use.

In the longitudinal direction the height of the ridges 3 varies sinusoidally between sites of the greatest and smallest height C, D. Moreover in the transverse direction, the ridges 3 have the profile of a bell-shaped curve. This is delimited at its base by the lines shown in FIG. 1. These lines are not recognizable on the product, because the ridges 3 merge into the top surface 4 of the cleaning body by avoiding an abrupt change of direction and sharp edges. Furthermore, at the crossing points, the limiting surfaces of the ridges merge into one another in a rounded-off fashion. Thus, the regions of varying heights C, D of the ridges 3 again follow each other regularly in every direction, with the individual ridges 3 nevertheless enclosing bowl-shaped recesses 5 in the manner of a waffle pattern. The base of the recesses 5 determines the position of the top surface above which rise the ridges 3.

The recesses 5 are suitable for taking up, in a largely pressure-free manner, relatively large amounts of dirt which are detached from a surface to be cleaned. Despite the exertion of considerable pressing forces, a rubbing-in action into the pore structure of the cleaning body is prevented, because these forces are absorbed predominantly by the ridges 3 and, particularly, by those parts of the ridges 3 in which they attain the greatest height C. Hence, after exceeding the lateral edge limit of the body to be cleaned, the detached dirt components readily fall out from the recesses 5, after which the original storage capacity is regained. In any case, a firm settling of such dirt components within the interior of the pore structure of the cleaning body is largely prevented.

The scrubbing surface 2 is coated in its entirety with a layer of cross-linked elastomeric polyurethane, which is applied in the course of an impregnation process and is then hardened and bonded with the scrubbing surface 2 in an undetachable manner. In this way its mechanical strength and, in particular, its abrasion resistance is considerably increased. In the transverse direction the coating is permeated by pores. This results in a good water permeability in the direction of the surface to be worked, which allows the amounts of water stored in the open-pored structure of the cleaning body to be readily displaced toward the front side of the scrubbing surface 2 by pressure exerted on the cleaning body, or to draw them, together with the detached dirt components, out of the scrubbing surface 2 during a cleaning process when the pressure is released.

Worked into the coating is an abrasive granulate which may consist of rubber particles and/or a scrubbing agent. In this way, even adhering dirt components can be eliminated from a surface to be cleaned without any difficulty.

The cleaning body shown in the drawing is provided with ridges 3 of the type according to the invention only in the region of a scrubbing surface 2. As a result the reverse side can be used to dry the surfaces that are already cleaned. In the embodiment shown, this side is formed of a lining of viscous sponge 6, which is particularly well suited for these purposes. By contrast, it is possible, if necessary, to provide this surface, or even additional surfaces of the cleaning body, with correspondingly or differently formed ridges 3. In such embodiments, the scrubbing surface 2 which is not being used momentarily is again completely freed from adhering dirt components through the milling movements of the cleaning body with another scrubbing surface 2' which occur during the normal cleaning process, as well as through the pressure-free absorption and outflow of water through the pore structure of the unused scrubbing surface, and it is made suitable for a renewed application, without any special effort being required for this purpose.

Figure 6:
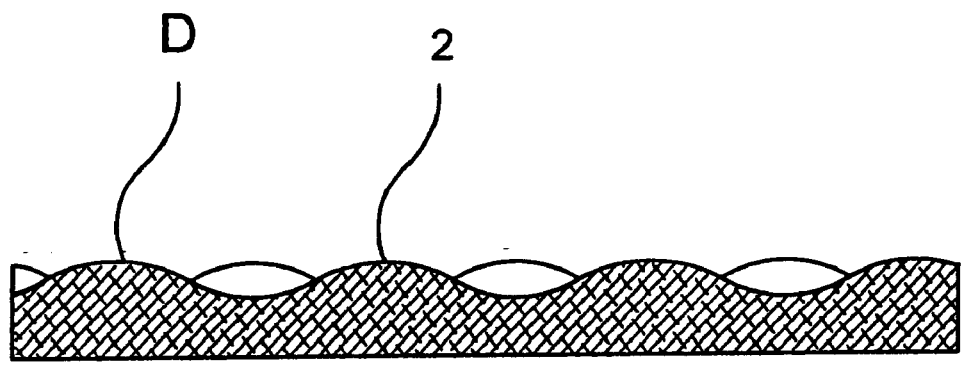
FIG. 6 and FIG. 7 show a cleaning body in cross-sectional representation, and in a view of the scrubbing surface, wherein perpendicularly intersecting ridges are all arranged obliquely to the longitudinal direction of the scrubbing body.
Figure 7:
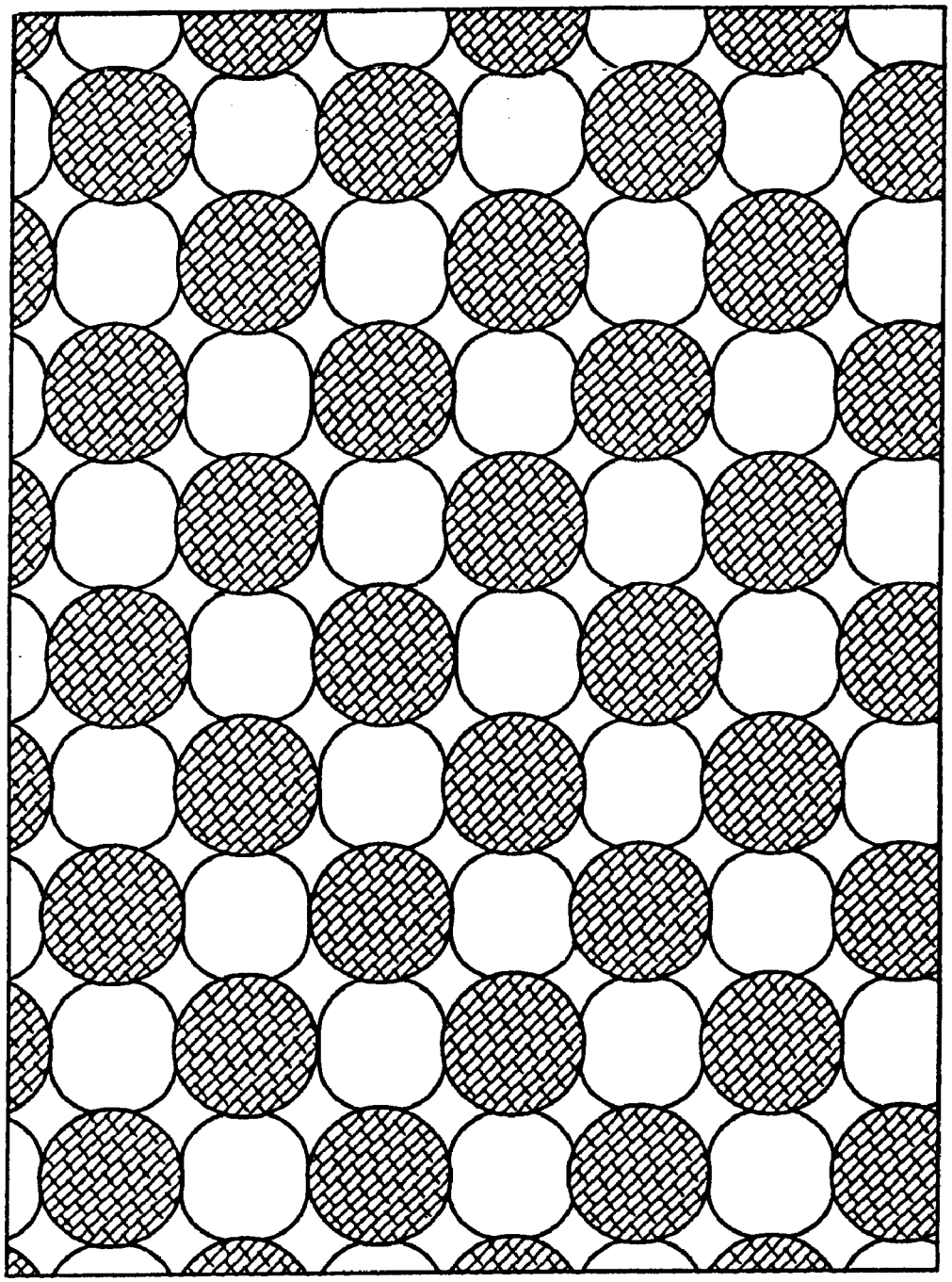

FIGS. 6 and 7 show a cleaning body in the form of a cleaning cloth made of foam which is produced homogeneously from a single foam block and is delimited on its lower side by a flat surface. The top side is formed of a scrubbing surface 2 which is structured analogously to the above-described surface, but whose perpendicularly intersecting ridge clusters are arranged obliquely to the longitudinal direction and at an angle of 45 degrees. Thus, the sites of greatest heights of the ridge 3, which follow one another in the longitudinal direction, are so disposed with respect to each other so that they fill up gaps. In this way, despite relatively great opposite distances between the sites of greatest height D of the ridges 3, a nearly gapless attack on the surface to be cleaned is attained in the operating direction which is transverse to the longitudinal direction.

If the cleaning body according to FIGS. 6 and 7 does not move over the surface to be cleaned in a way that is exactly parallel to its longitudinal direction, but is more or less rotated away from that direction, then an automatic improvement of the extent of mutual covering of the strips cleaned through the sites of greatest height D takes place. On normal performance of a cleaning process, the thus oblique correlation of the longitudinal direction of the ridges 3 with the direction of movement is almost always satisfied. Hence, within the framework of the present invention, an arrangement and design of the ridges 3 in accordance with FIGS. 6 and 7 is preferred.

What is claimed is:

1. A method for cleaning a surface, comprising contacting said surface with a liquid-absorbent cleaning body, said cleaning body comprising a body portion, said body portion being composed of a body portion material;

said body portion including a scouring surface, said scouring surface comprising a plurality of spaced apart ridges, said scouring surface being provided with a flexible liquid-permeable coating that is comprised of a coating material, said coating material being relatively more resistant to abrasion than said body portion material, said coating including particles of a scrubbing agent.

2. A method according to claim 1, said coating material comprising a polyurethane.

3. A method for cleaning a surface, comprising contacting said surface with a liquid-absorbent cleaning body, said cleaning body comprising a body portion, said body portion being composed of a body portion material, said body portion having a major longitudinal direction, said body portion being provided with a scouring surface having a flexible liquid-permeable coating, said coating surface being composed of a polyurethane, said coating being relatively more resistant to abrasion than said body portion material, said body portion including a plurality of space apart ridges, each of said ridges extending in a direction that is generally oblique to said major longitudinal direction of said body portion, each of said ridges being delimited by inclined surfaces, said body portion having a face opposing said scouring surface, said face being delimited by a flat surface of said body section.

4. A method according to claim 3, said ridges being straight.

5. A method according to claim 3, said ridges being serpentine.

6. A method according to claim 3, said inclined surfaces having a curvature.

7. A method according to claim 3, whereas each of said ridges has a maximum height, wherein the ratio of the distance between the midpoint of adjacent ridges to said maximum height ranges from about 4 to 12.

8. A method according to claim 7, wherein said ratio ranges from 6 to 9.

9. A method according to claim 3, wherein said coating has a thickness of from 2–5 mm.

10. A method for cleaning a surface, comprising contacting said surface with a liquid-absorbent cleaning body, said cleaning body comprising a body portion, said body portion being composed of a body portion material, said body portion having a major longitudinal direction, said body portion being provided with a scouring surface having a flexible liquid-permeable coating, said coating having a thickness of from 2–5 mm and comprising a polyurethane, said coating including particles of a scrubbing agent, said coating being relatively more resistant to abrasion than said body portion material, said body portion including a plurality of spaced apart ridges, each of said ridges extending in a direction that is generally oblique to said major longitudinal direction of said body portion, each of said ridges being delimited by curved inclined surfaces, wherein each of said ridges has a maximum height, wherein the ratio of the distance between the midpoint of adjacent ridges to said maximum height ranges from about 4 to 12.

11. A method according to claim 10, said ridges being straight.

12. A method according to claim 10, said ridges being serpentine.

13. A method according to claim 10, wherein said ratio ranges from 6 to 9.

14. A method for cleaning a surface, comprising contacting said surface with a liquid-absorbent cleaning body, said cleaning body comprising a body portion, said body portion being composed of a body portion material;

said body portion including a scouring surface, said scouring surface comprising a plurality of spaced apart ridges, said scouring surface being provided with a flexible liquid-permeable coating that is comprised of a coating material, said coating material being relatively more resistant to abrasion than said body portion material.

* * * * *